(12) United States Patent
Weissman et al.

(10) Patent No.: US 8,877,765 B2
(45) Date of Patent: Nov. 4, 2014

(54) HIGHLY SOLUBLE PYRIMIDO-DIONE-QUINOLINE COMPOUNDS AND THEIR USE IN THE TREATMENT OF CANCER

(75) Inventors: Allan M. Weissman, Bethesda, MD (US); Yili Yang, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1197 days.

(21) Appl. No.: 12/304,980

(22) PCT Filed: Jun. 13, 2007

(86) PCT No.: PCT/US2007/013952
§ 371 (c)(1),
(2), (4) Date: Oct. 28, 2009

(87) PCT Pub. No.: WO2007/146375
PCT Pub. Date: Dec. 21, 2007

(65) Prior Publication Data
US 2010/0056549 A1 Mar. 4, 2010

Related U.S. Application Data

(60) Provisional application No. 60/813,946, filed on Jun. 14, 2006.

(51) Int. Cl.
*A61K 31/519* (2006.01)
*C07D 239/70* (2006.01)
*C07D 471/04* (2006.01)

(52) U.S. Cl.
CPC ............ *C07D 471/04* (2013.01); *C07D 239/70* (2013.01); *A61K 31/519* (2013.01)
USPC .......................................... 514/267; 544/250

(58) Field of Classification Search
USPC .......................................... 514/267; 544/250
See application file for complete search history.

(56) References Cited

FOREIGN PATENT DOCUMENTS

| JP | 3081276 | * | 5/1991 | ........... C07D 471/04 |
|---|---|---|---|---|
| WO | 2004005464 | A | 1/2004 | |
| WO | WO 2004/005464 | * | 1/2004 | |
| WO | 2006015369 | A | 2/2006 | |
| WO | WO 2006/015369 | * | 2/2006 | ............... C12Q 1/68 |

OTHER PUBLICATIONS

Tanaka, et al., On Mechanistic Aspects of 5-deazaflavin-dependent Dehydrogenation of Alcohol, Journal of Heterocyclic Chemistry 24(1), 251-4 (1987).*
Kimachi, et al., New Synthesis of 5-amino-5-deazaflavin Derivatives by Direct Coupling of 5-deazaflavins and Amines, 29(4), 763-5 (1992).*
Sorscher, et al., Activators of Viral Gene Expression in Polarized Epithelial Monolayers Identified by Rapid-throughput Drug Screening, Gene Therapy, 13, 781-788 (2006).*
Taylor, et al., P53 Mutation and MDM2 Amplification Frequency in Pediatric Rhabdomyosarcoma Tumors and Cell Lines, Medical and Pediatric Oncology, vol. 35, No. 2, pp. 96-103 (2000).*
JP03081276A; Apr. 5, 1994; Abstract Only (1 page).
International Search Report; International Application No. PCT/US2007/013952; International Filing Date Jun. 13, 2007; 4 pages.
Yang et al., "Small molecule inhibitors of HDM2 ubiquitin ligase activity stabilize and activate p53 in cells" Cancer Cell: Jun. 2005, vol. 7, pp. 547-559.
Ladanyi, et al., "MDM2 Gene Amplification in Metastatic Osteosarcoma," Cancer Research 53: 16-18 (1993).
Nenutil, et al., "Discriminating functional and non-functional P53 in human tumours by p53 and MDM2 immunohistochemistry," Journal of Pathology 207: 251-259 (2005).
Woods, et al., "Regulation of P53 Function," Experimental Cell Research 264: 56-66 (2001).

* cited by examiner

*Primary Examiner* — Erich A Leeser
(74) *Attorney, Agent, or Firm* — Cantor Colburn LLP

(57) ABSTRACT

The present invention features pyrimido-dione-quinoline compounds having improved solubility, pharmaceutical compositions of substituted pyrimido-dione-quinoline compounds and methods of treating a patient suffering from cancer, the method comprising administering to a patient one or more pyrimido-dione-quinoline compounds of the invention.

21 Claims, 7 Drawing Sheets

Compound 1 selectively stabilizes Hdm2 in MEFs.
ALLN, 1, 3, and 4 were used at 50 µM, whereas 20 µM of 4 was used.

Compound 1 prevents Hdm2-mediated p53 degradation in U2OS cells.

Compound 1 preferentially kills tumor cells expressing wild type p53

HIGHLY SOLUBLE PYRIMIDO-DIONE-QUINOLINE COMPOUNDS AND THEIR USE IN THE TREATMENT OF CANCER

RELATED APPLICATION

This application claims the benefit of U.S. provisional patent application Ser. No. 60/813,946, filed Jun. 14, 2006, the disclosure of which is incorporated herein in its entirety by this reference.

GOVERNMENT SUPPORT

Research supporting this application was carried out by the United States of America as represented by the Secretary, Department of Health and Human Services.

BACKGROUND OF THE INVENTION

1. Field of the Invention

The present invention is directed to pyrimido-dione-quinoline compounds having an improved water solubility, and methods and pharmaceutical compositions that comprise such compounds. Compounds of the invention can be effective to modulate the function of the ubitquitylation system, regulate p53 and Mdm2 stability and activity, as well as to act as therapeutic agents in a variety of indications, particularly to treat cancer.

2. Background

The development of cancer can depend on the accumulation of specific genetic alterations that allow aberrant cell proliferation, including growth of tumor cells. Protection from such aberrant growth is provided by several mechanisms that work by inducing apoptotic cell death in cells undergoing oncogenic changes. Therefore, for a tumor cell to survive, it must acquire genetic alterations that perturb the link between abnormal growth and cell death. The p53 tumor suppressor protein can induce apoptotic cell death and plays a pivotal role in tumor suppression. Wild type p53 functions as a transcriptional regulator to coordinately control multiple pathways in cell cycling, apoptosis, and angiogenesis.

Loss of the ability to induce p53 or other loss of p53 activity can lead to uncontrolled cell proliferation of the affected cells and tumor growth. In approximately 50% of human cancers, a wild type p53 gene is nevertheless retained. In such cancers, the defect that frequently occurs is a failure to stabilize and activate p53 to thereby prevent tumor development.

The Mdm2 protein plays an important role in targeting the degradation of p53 in normal cells to allow normal growth and development. In particular, inhibition of Mdm2 is required to allow activation of a p53 response. In tumors with wild type p53, defects can occur that lead to increased Mdm2 activity, whereby p53 function cannot be induced.

Ubiquitin-mediated proteolysis is an important pathway of non-lysosomal protein degradation that controls the timed destruction of a number of cellular regulatory proteins including p53. See Pagano, 1997 FASEB J. 11:1067. Ubiquitin is an evolutionary highly conserved 76-amino acid polypeptide which is abundantly present in eukaryotic cells. The ubiquitin pathway leads to the covalent attachment of poly-ubiquitin chains to target substrates which are then degraded by a multi-catalytic proteasome complex.

A number of the steps of regulating protein ubiquitination are known. In particular, initially the ubiquitin activating enzyme (E1) forms a high energy thioester linkage with ubiquitin. Ubiquitin is then transferred to a reactive cysteine residue of one of many ubiquitin conjugating enzymes known as Ubc or ubiquitin E2 enzymes. The final transfer of ubiquitin to a target protein involves one of many ubiquitin protein ligases (E3s). Mdm2 is such a ubiquitin ligase that mediates the transfer of ubiquitin to p53.

It thus would be desirable to have new compounds that have use in treatment of undesired cell proliferation, including in treatment against cancer cells. It would be especially desirable to have new compounds that could modulate or stabilize p53 activity.

SUMMARY OF THE INVENTION

The instant invention provides a compound according to Formula I:

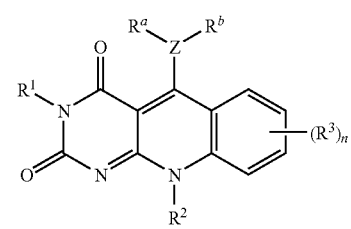

wherein:

$R^1$ is selected from the group consisting of hydrogen, optionally substituted alkyl, optionally substituted alkenyl, optionally substituted alkynyl, optionally substituted carbocyclic aryl, optionally substituted heteroaryl, optionally substituted cycloalkyl, or optionally substituted heteroalicyclic;

$R^2$ is selected from the group consisting of optionally substituted alkyl, optionally substituted cycloalkyl, or optionally substituted heteroalicyclic;

$R^3$ is, for each occurrence, selected from the group consisting of H, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl amino, optionally substituted cycloalkyl, optionally substituted heteroalicyclic, optionally substituted aminoalkyl, —$OR^a$, —$NR^aR^b$, —$S(O)_qR^a$, —$C(O)R^a$, —$OC(O)R^a$, —$NR^aC(O)R^a$, —$C(S)R^a$, —$OC(S)R^a$, —$SC(S)R^a$, —$NR^aC(S)R^a$, —$C(NR^a)R^a$, —$OC(NR^a)R^a$, —$SC(NR^a)R^a$, —$NR^aSO_2R^c$, —$OS(O)_2R^a$;

Z is selected from N, O, or $S(O)_q$; wherein $R_a$ is absent if not allowed;

$R^a$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, hydroxylalkyl, alkylcarbonylalkyl, mercaptoalkyl, aminoalkyl, sulfonylalkyl, sulfonylaryl, or thioalkoxy;

$R^b$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, —(CH$_2$)$_n$OR$^c$, —(CH$_2$)$_n$SR$^c$, —(CH$_2$)$_n$NR$^c$R$^c$, hydroxylalkyl, alkylcarbonylalkyl, mercaptoalkyl, aminoalkyl, sulfonylalkyl, sulfonylaryl, or thioalkoxy;

R$^c$, for each instance is independently selected from the group consisting of H or an optionally substituted alkyl;

n is an integer from 0 to 3;

q is an integer from 0 to 2;

and pharmaceutically acceptable salts, solvate, or hydrate thereof.

In another aspect, the invention provides a compound according to Formula II:

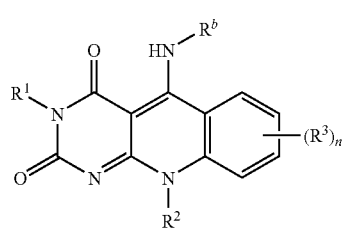

wherein:

R$^1$ is selected from the group consisting of optionally substituted alkyl, optionally substituted carbocyclic aryl, optionally substituted heteroaryl, or optionally substituted cycloalkyl;

R$^2$ is optionally substituted alkyl;

R$^3$ is, for each occurance, selected from the group consisting of hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl amino, optionally substituted cycloalkyl, optionally substituted heteroalicyclic, optionally substituted aminoalkyl, —OR$^a$, —NR$^a$R$^b$, —S(O)$_q$R$^a$, —C(O)R$^a$, —OC(O)R$^a$, —NR$^a$C(O)R$^a$, —C(S)R$^a$, —OC(S)R$^a$, —SC(S)R$^a$, —NR$^a$C(S)R$^a$, —C(NR$^a$)R$^a$, —OC(NR$^a$)R$^a$, —SC(NR$^a$)R$^a$, —NR$^a$SO$_2$R$^c$, —OS(O)$_2$R$^a$;

R$^a$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, hydroxylalkyl, alkylcarbonylalkyl, mercaptoalkyl, aminoalkyl, sulfonylalkyl, sulfonylaryl, or thioalkoxy;

R$^b$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, —(CH$_2$)$_n$OR$^c$, —(CH$_2$)$_n$SR$^c$, —(CH$_2$)$_n$NR$^c$R$^c$, hydroxylalkyl, alkylcarbonylalkyl, mercaptoalkyl, aminoalkyl, sulfonylalkyl, sulfonylaryl, or thioalkoxy;

R$^c$, for each instance is independently selected from the group consisting of H or an optionally substituted alkyl;

n is an integer from 0 to 3;

q is an integer from 0 to 2;

and pharmaceutically acceptable salts, solvate, or hydrate thereof.

In another aspect, the invention provides a method of treating a subject suffering from or susceptible to a cell proliferative disorder or disease comprising: administering to the subject an effective amount of a compound or pharmaceutical composition of formula I or formula II.

In another aspect, the invention provides a method of treating or preventing cancer comprising administering a compound or pharmaceutical composition of formula I or II, to a subject suffering from or susceptible to cancer.

In still another aspect, the invention provides a method of activating p53 mediated tumor suppression comprising contacting administering to mammalian cells a compound or pharmaceutical composition of formula I or II.

In certain aspects, the invention provides a method of treating against undesired cell proliferation comprising: administering to a mammal suffering from or susceptible to cancer the compound 5-(3-Dimethylamino-propylamino)-3,10-dimethyl-10H-pyrimido[4,5-b]quinoline-2,4-dione, and pharmaceutically acceptable salts thereof.

In another aspect, the invention provides a method of modulating HDM2 autoubiquitination in a subject, the method comprising the step of administering to the subject a compound of formula I or II, in an amount and under conditions sufficient to modulate HDM2 autoubiquitination.

DETAILED DESCRIPTION OF THE INVENTION

Definitions

Figure 1:
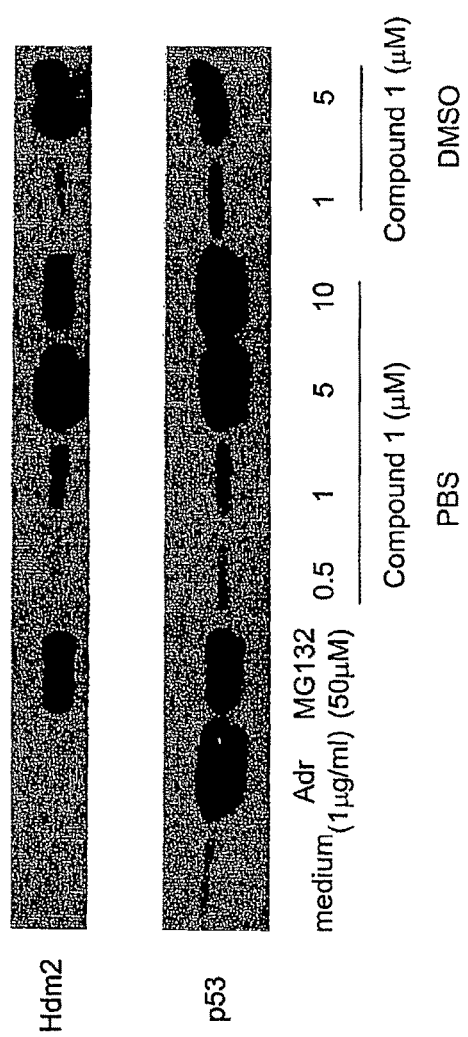
FIG. 1 shows the accumulation of both Hdm2 and p53 when compound 1 is dissolved in either phosphate buffered saline (PBS) or in dimethyl sulfoxide (DMSO).

Before a further description of the present invention, and in order that the invention may be more readily understood, certain terms are first defined and collected here for convenience.

As used herein, "Hdm2" refers to the human homologue of murine "Mdm2," which is a transformed 3T3 cell double minute 2, p53 binding protein (mouse). The terms "Hdm2" and "Mdm2" are used interchangeably.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical. Preferred alkoxy groups of compounds of the invention include groups having one or more oxygen linkages and from 1 to about 12 carbon atoms, more preferably from 1 to about 8 carbon atoms, and still more preferably 1, 2, 3, 4, 5 or 6 carbon atoms.

The term "ester" refers to a —C(O)O—R, where R is defined herein. An "amido" is an —C(O)NH$_2$, and an "N-alkyl-substituted amido" is of the formula C(O)NHR, where R is defined herein.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

The term "cycloalkyl" refers to a hydrocarbon 3-8 membered monocyclic or 7-14 membered bicyclic ring system having at least one non-aromatic. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cyclic" or similar term refers to a hydrocarbon 3-8 membered monocyclic or 7-14 membered bicyclic ring system having at least one non-aromatic ring, wherein the non-aromatic ring has some degree of unsaturation. Cyclic groups may be optionally substituted with one or more substituents. In one embodiment, 0, 1, 2, 3, or 4 atoms of each ring of a cyclic group may be substituted by a substituent. Examples of cycicl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

Carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,4-substituted phenyl, and 2,4-substituted phenyl; and substituted naphthyl, including naphthyl substituted at the 5, 6 and/or 7 positions.

As used herein, the term "aralkyl" means an aryl group that is attached to another group by a ($C_1$-$C_6$)alkylene group. Aralkyl groups may be optionally substituted, either on the aryl portion of the aralkyl group or on the alkylene portion of the aralkyl group, with one or more substituent. Representative aralkyl groups include benzyl, 2-phenyl-ethyl, naphth-3-yl-methyl, methylenenaphthyl (—CH$_2$-naphthyl), and the like. Other aralkyl groups of compounds of the invention include single and multiple ring compounds, including multiple ring compounds that contain separate and/or fused aryl groups.

As used herein, the term "alkylene" refers to an alkyl group that has two points of attachment. The term "($C_1$-$C_6$)alkylene" refers to an alkylene group that has from one to six carbon atoms. Non-limiting examples of alkylene groups include methylene (—CH$_2$—), ethylene (—CH$_2$CH$_2$—), n-propylene (—CH$_2$CH$_2$CH$_2$—), isopropylene (—CH$_2$CH(CH$_3$)—), and the like.

The term "arylalkoxy" refers to an alkoxy substituted with aryl.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole.

As used herein, the term "heteroaralkyl" or "heteroaralkyl" means a heteroaryl group that is attached to another group by a ($C_1$-$C_6$)alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

Heteroalicyclic groups of compounds of the invention contain one or more N, O or S atoms and include, e.g., tetrahydrofuranyl, thienyl, tetrahydropyranyl, piperidinyl, morpholino and pyrrolidinyl groups.

The term "heterocycloalkyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents.

In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirene.

The term "heterocyclic" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclic groups may be optionally substituted with one or more substituents. In one embodiment, 0, 1, 2, 3, or 4 atoms of each ring of a heterocyclic group may be substituted by a substituent. Examples of these groups include thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin, 1,4-dioxin, 1,4-dithiin, 1H-pyranyl, oxathiepinyl, 5H-1,4-dioxopinyl, 5H-1,4-dithiepinyl, 6H-isoxazolo[2,3-d]1,2,4-oxadiazolyl, 7aH-oxazolo[3,2-d]1,2,4-oxadiazolyl, and the like.

Suitable heteroalicyclicalkyl groups of compounds of the invention include single and multiple ring compounds, where such groups are substituted onto an alkyl linkage. More preferably, a heteroalicylicalkyl group contains at least one ring that has 3 to 8 ring members from 1 to 3 hetero (N, O or S) atoms, substituted onto an alkyl linkage. Suitable heteroalicyclic groups substituted onto an alkyl linkage include, e.g. tetrahydrofuranyl, thienyl, tetrahydropyranyl, piperidinyl, morpholino and pyrrolidinyl groups.

Suitable heteroaralkyl groups of compounds of the invention include single and multiple ring compounds, including multiple ring compounds that contain separate and/or fused heteroaromatic groups, where such groups are substituted onto an alkyl linkage. More preferably, a heteroaralkyl group contains a heteroaromatic group that has 1 to 3 rings, 3 to 8 ring members in each ring and from 1 to 3 hetero (N, O or S) atoms, substituted onto an alkyl linkage. Suitable heteroaromatic groups substituted onto an alkyl linkage include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole.

The term "alkylamino" refers to an amino substituent which is further substituted with one or two alkyl groups. The term "aminoalkyl" refers to an alkyl substituent which is further substituted with one or more amino groups. Preferred aminoalkyl groups include those groups having one or more primary, secondary and/or tertiary amine groups, and from 1 to about 12 carbon atoms, more preferably 1 to about 8 carbon atoms, still more preferably 1, 2, 3, 4, 5, or 6 carbon atoms.

The term "mercapto" refers to a —SH group. The term "mercaptoalkyl" refers to an alkyl substituent which is further substituted with one or more mercapto groups.

Alkylthio groups of compounds of the invention include those groups having one or more thioether linkages and from 1 to about 12 carbon atoms, more preferably from 1 to about 8 carbon atoms, and still more preferably 1, 2, 3, 4, 5, or 6 carbon atoms.

The term "hydroxyalkyl" or "hydroxylalkyl" refers to an alkyl substituent which is further substituted with one or more hydroxyl groups.

The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —(O)-alkyl. Preferred alkylsulfinyl groups of compounds of the invention include those groups having one or more sulfoxide (SO) groups and from 1 to about 12 carbon atoms, more preferably from 1 to about 8 carbon atoms, and still more preferably 1, 2, 3, 4, 5, or 6 carbon atoms. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1, 2, 3, 4, 5 or 6 carbon atoms.

The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

The term "N-oxides" refers to one or more nitrogen atoms, when present in an aromatic ring nitrogen-containing compound, that are in N-oxide oxidation form, i.e., N→O.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, or heterocycloalkyl group) is replaced with any desired group that do not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cycloalkyl, heterocycloalkyl, wherein alkyl, alkenyl, alkyloxy, aryl, heteroaryl, cycloalkyl, and heterocycloalkyl are optionally substituted with alkyl, aryl, heteroaryl, halogen, hydroxyl, amino, mercapto, cyano, nitro, oxo (=O), thioxo (=S), or imino (=NR).

In other embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents of an alkyl, alkenyl, alkynyl, aryl, aralkyl, heteroaryl, heteroaralkyl, cycloalkyl, and heterocycloalkyl include, without limitation halogen, CN, NO$_2$, OR$^{15}$, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, (=O), (=S), (=NR$^{15}$), C(O)OR$^{15}$, C(O)NR$^{15}$R$^{16}$, OC(O) NR$^{15}$R$^{16}$, NR$^{15}$C(O)NR$^{15}$R$^{16}$, C(NR$^{16}$)NR$^{15}$R$^{16}$, NR$^{15}$C (NR$^{16}$)NR$^{15}$R$^{16}$, S(O)$_2$NR$^{15}$R$^{16}$, R$^{17}$, C(O)H, C(O)R$^{17}$, NR$^{15}$C(O)R$^{17}$, Si(R$^{15}$)$_3$, OSi(R$^{15}$)$_3$, Si(OH)$_2$R$^{15}$, B(OH)$_2$, P(O)(OR$^{15}$)$_2$, S(O)R$^{17}$, or S(O)$_2$R$^{17}$. Each R$^{15}$ is independently hydrogen, C$_1$-C$_6$ alkyl optionally substituted with cycloalkyl, aryl, heterocycloalkyl, or heteroaryl. Each R$^{16}$ is independently hydrogen, C$_3$-C$_6$ cycloakyl, aryl, heterocycloalkyl, heteroaryl, C$_1$-C$_4$ alkyl or C$_1$-C$_4$ alkyl substituted with C$_3$-C$_6$ cycloalkyl, aryl, heterocycloalkyl or heteroaryl. Each R$^{17}$ is independently C$_3$-C$_6$ cycloalkyl, aryl, heterocycloalkyl, heteroaryl, C$_1$-C$_4$ alkyl or C$_1$-C$_4$ alkyl substituted with C$_3$-C$_6$ cycloalkyl, aryl, heterocycloalkyl or heteroaryl. Each C$_3$-C$_6$ cycloalkyl, aryl, heterocycloalkyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, COOH, C(O)OC$_1$-C$_4$ alkyl, NH$_2$, C$_1$-C$_4$ alkylamino, or C$_1$-C$_4$ dialkylamino.

As discussed above, various substituent groups (R$^1$, R$^2$, R$^3$, and R$^4$) of Formulae I and II may be optionally substituted. A "substituted" R$^1$, R$^2$, R$^3$, and R$^4$ group or other substituent may be substituted by other than hydrogen at one or more available positions, typically 1 to 3 or 4 positions, by one or more suitable groups such as those disclosed herein. Suitable groups that may be present on a "substituted" R$^1$, R$^2$, R$^3$, and R$^4$ group or other substituent include e.g. halogen such as fluoro, chloro, bromo and iodo; cyano; hydroxyl; nitro; azido; alkanoyl such as a C$_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons, particularly phenyl (e.g. an R group being a substituted or unsubstituted biphenyl moiety); aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, ape, monkey, or human), and more particularly a human. In one embodiment, the subject is an immunocompromised or immunosuppressed mammal, particularly a human (e.g., an HIV infected patient). In another embodiment, the subject is a mammal suffering from undesired cell growth, particularly a cancer, such as a human suffering from cancer.

Compounds of the Invention

In one aspect, the invention provides a compound according to Formula I:

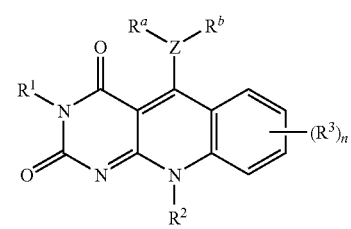

I wherein:

R$^1$ is selected from the group consisting of hydrogen, optionally substituted alkyl, optionally substituted alkenyl, optionally substituted alkynyl, optionally substituted carbocyclic aryl, optionally substituted heteroaryl, optionally substituted cycloalkyl, or optionally substituted heteroalicyclic;

R$^2$ is selected from the group consisting of optionally substituted alkyl, optionally substituted cycloalkyl, or optionally substituted heteroalicyclic;

R$^3$ is, for each occurance, selected from the group consisting of H, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl amino, optionally substituted cycloalkyl, optionally substituted heteroalicyclic, optionally substituted aminoalkyl, —OR$^a$, —NR$^a$R$^b$, —S(O)$_q$R$^a$, —C(O)R$^a$, —OC(O)R$^a$, —NR$^a$C(O)R$^a$, —C(S)R$^a$, —OC(S)R$^a$, —SC(S)R$^a$, —NR$^a$C(S)R$^a$, —C(NR$^1$)R$^a$, —OC(NR$^1$)R$^a$, —SC(NR$^1$)R$^a$, —NR$^a$SO$_2$R$^c$, —OS(O)$_2$R$^a$;

Z is selected from N, O, or S(O)$_q$; wherein R$_a$ is absent if not allowed;

R$^a$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, hydroxylalkyl, alkylcarbonylalkyl, mercaptoalkyl, aminoallyl, sulfonylalkyl, sulfonylaryl, or thioalkoxy;

R$^b$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, —(CH$_2$)$_n$OR$^c$, —(CH$_2$)$_n$SR$^c$, —(CH$_2$)$_n$NR$^c$R$^c$, hydroxylalkyl, alkylcarbonylalkyl, mercaptoalkyl, aminoalkyl, sulfonylalkyl, sulfonylaryl, or thioalkoxy;

R$^c$, for each instance is independently selected from the group consisting of H or an optionally substituted alkyl;

n is an integer from 0 to 3;

q is an integer from 0 to 2;

and pharmaceutically acceptable salts, solvate, or hydrate thereof.

In another aspect, the invention provides a compound according to Formula II:

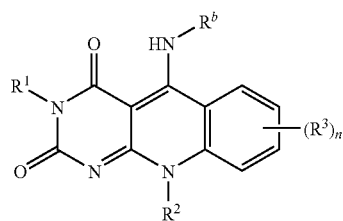

II wherein:

R$^1$ is selected from the group consisting of optionally substituted alkyl, optionally substituted carbocyclic aryl, optionally substituted heteroaryl, or optionally substituted cycloalkyl;

R$^2$ is optionally substituted alkyl;

R$^3$ is, for each occurance, selected from the group consisting of hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl-amino, optionally substituted cycloalkyl, optionally substituted heteroalicyclic, optionally substituted aminoalkyl, —OR$^a$, —NR$^a$R$^b$, —S(O)$_q$R$^a$, —C(O)R$^a$, —OC(O)R$^a$, —NR$^a$C(O)R$^a$, —C(S)R$^a$, —OC(S)R$^a$, —SC(S)R$^a$, —NR$^a$C(S)R$^a$, —C(NR$^a$)R$^a$, —OC(NR$^a$)R$^a$, —SC(NR$^1$)R$^a$, —NR$^a$SO$_2$R$^c$, —OS(O)$_2$R$^a$;

R$^a$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, hydroxylalkyl, alkylcarbonylalkyl, mercaptoalkyl, aminoalkyl, sulfonylalkyl, sulfonylaryl, or thioalkoxy;

R$^b$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, —(CH$_2$)$_n$OR$^c$, —(CH$_2$)$_n$SR$^c$, —(CH$_2$)$_n$NR$^c$R$^c$, hydroxylalkyl, alkylcarbonylalkyl, mercaptoalkyl, aminoalkyl, sulfonylalkyl, sulfonylaryl, or thioalkoxy;

R$^c$, for each instance is independently selected from the group consisting of H or an optionally substituted alkyl;

n is an integer from 0 to 3;

q is an integer from 0 to 2;

and pharmaceutically acceptable salts, solvate, or hydrate thereof.

In certain embodiments, the invention provides a compound of formula I or II, wherein R$^1$ is an optionally substituted alkyl. In further embodiments, R$^1$ is methyl.

In another embodiment, the invention provides a compound of formula I, wherein Z is N. In still another embodiment, the invention provides a compound wherein R$^a$, for each instance, is independently H, an optionally substituted alkyl, an optionally substituted aryl, or an optionally substituted heteroaryl. In a further embodiment, R$^a$ is H.

In certain embodiments, the invention provides a compound wherein R$^b$, for each instance is independently selected from the group consisting of —(CH$_2$)$_n$OR$^c$, —(CH$_2$)$_n$SR$^c$, —(CH$_2$)$_n$NR$^c$R$^c$, hydroxylalkyl, alkylcarbonylalkyl, mercaptoalkyl, aminoalkyl, sulfonylalkyl, sulfonylaryl, or thioalkoxy. In a further embodiment, R$^b$ is —(CH$_2$)$_n$NR$^c$R$^c$.

In yet another embodiment, the invention provides a compound wherein each R$^c$ is independently an optionally substituted alkyl. In a further embodiment, R$^c$ is methyl.

In certain embodiments, the invention provides a compound wherein R$^2$ is selected from the group consisting of optionally substituted alkyl, optionally substituted cycloalkyl, or optionally substituted heteroalicyclic. In a further embodiment, R$^2$ is optionally substituted alkyl. In still another further embodiment, R$^2$ is methyl.

In another embodiment, the invention provides a compound, wherein the compound is soluble in a solvent. In certain embodiments, the solubility of the compound is about 1.0 mM to about 100 mM. In certain embodiments, the solubility of the compound is about 25 mM to about 60 mM. In another embodiment, the compound is soluble in an aqueous solvent or an organic solvent. In a further embodiment, the solvent is water or PBS. In another embodiment, the solvent is DMSO.

In certain embodiments, the invention provides a compound wherein the compound is capable of stabilizing p53 in transformed cells.

In still another embodiment, the invention provides a compound, wherein the compound is capable of inhibiting HDM2 activity.

In yet another embodiment, the invention provides a compound, wherein the compound provides at least about 20 percent decreased self-ubiquitiylation of HDM2 relative to a control in a standard HDM2 activity in vitro assay.

A preferred compound is 5-(3-Dimethylamino-propylamino)-3,10-dimethyl-10H-pyrimido[4,5-b]quinoline-2,4-dione (1):

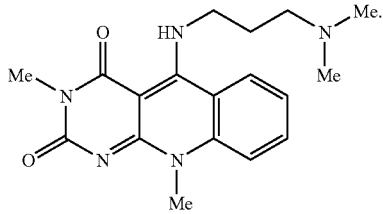 [SMILES: CN(C)CCCNc1c2c(=O)n(C)c(=O)nc-2n(C)c2ccccc12]

Also preferred is the hydrochloride salt of compound 1:

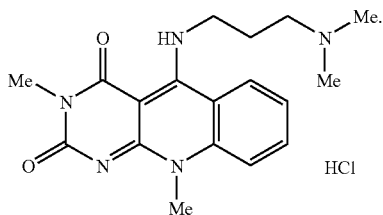 [SMILES: CN(C)CCCNc1c2c(=O)n(C)c(=O)nc-2n(C)c2ccccc12 ; Cl]

More specifically, the invention describes the water soluble compound 5-(3-Dimethylamino-propylamino)-3,10-dimethyl-10H-pyrimido[4,5-b]quinoline-2,4-dione, hydrochloride, that inhibits the degradation of the tumor suppressor p53. The invention also describes water soluble compounds of formula I and II, that inhibit the degradation of the tumor suppressor p53. Compound 1, compounds of formula I or II, and salts thereof, are more effective in reactivating p53 compared to other deazaflavin compounds due to their increased potency which is a result of the increased water solubility.

The present invention also is directed to a method of improving the solubility of compounds of formula I, II, or compound 1 and salts of compound 1. The present invention improves the solubility and bioavailability of compounds of Formula I and II, at least by conversion of the compounds of the invention into a corresponding hydrochloride salt.

The water solubility of compounds of formula I or II, or compound 1 or its hydrochloride salt, is from about 1.0 mM to about 100 mM. In certain embodiments, the solubility is from about 5.0 mM to about 75 mM. In further embodiments, the solubility is from about 15 mM to about 70 mM. In certain embodiments, the solubility is from about 25 mM to about 60 mM. In certain embodiments, the solubility is about 50 mM. The increased solubility is observed in solvents selected from the following: water, buffered water solutions (including phosphate buffered saline (PBS)), alcohols (including methanol, ethanol, propanol, isopropanol, butanol, isobutanol, sec-butanol, tert-butanol, pentanol, hexanol, phenol, 2,2,2-trifluoroethanol, and others), dimethyl sulfoxide (DMSO), dimethyl formamide (DMF), formamide, formic acid, glycerol, ethylene glycol, ammonia, acetic acid, propyl amine, butyl amine, diethyl amine, acetonitrile, pyridine, pyrrolidinone, acetone, methylene chloride, tetrahydrofuran (THF), methyl tert-butyl ether (MTBE), diethyl ether, chloroform, ethyl acetate, diglyme, glyme, triethylamine, toluene, benzene, and dioxane.

The recitation of a listing of chemical groups in any definition of a variable herein includes definitions of that variable as any single group or combination of listed groups.

In another aspect, the invention includes compounds that can interact with E1 and/or E2 enzymes. Compounds that inhibit at E1 and/or E2 levels are useful drug candidates that indirectly interfere with the activity of ubiquitin ligases, particularly MDM2. Since interactions between E1 and E2 share similarities to those between E2 and E3, and compounds of the invention may also inhibit loading of E2 by E1, and thereby, inhibit the activity of ubiquitin ligases such as MDM2.

Combinations of substituents and variables envisioned by this invention are preferably those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating diseases, disorders or symptoms thereof). The compounds produced by the methods herein can be incorporated into compositions, including solutions, capsules, crèmes, or ointments for administration to a subject (e.g., human, animal). Such compositions (e.g., pharmaceuticals) are useful for providing to the subject desirable health or other physiological benefits that are associated with such compounds.

The compounds of this invention include the compounds themselves, as well as their salts, solvate, hydrate, polymorph, or prodrugs, if applicable. The compounds include "pharmaceutically acceptable salts" and refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

The compounds herein may contain one or more asymmetric centers and thus occur as racemates and racemic mixtures, single enantiomers, individual diastereomers and diastereomeric mixtures. Compounds suitable for use in the methods of the present invention include any and all different single pure isomers and mixtures of two or more isomers. The term isomers is intended to include diastereoisomers, enantiomers, regioisomers, structural isomers, rotational isomers, tautomers, and the like. All such isomeric forms of these compounds are expressly included in the present invention.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds herein are expressly included in the present invention. All crystal forms and polymorphs of the compounds described herein are expressly included in the present invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with a enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Compounds of the invention can be readily prepared by known synthetic methods. For example, a compound of Formula I may be prepared by cyclocondensation of a 6-(N-alkylamino)-uracil and a 2-halo-benzaldehyde to form 10-alkyl-pyrimido-dione-quinoline compounds. In other embodiments, various compounds of the invention can be readily prepared having a variety of functionalized aryl groups by synthesizing pyrimido-dione-quinoline compounds from 6-aminouracil and a 2-halo-benzaldehyde compound. Subsequent alkylation at the 10 position may be carried out in any convenient manner known to a chemist of ordinary skill in the art.

As discussed above, it has been found that 7-nitro-5-deazaflavin compounds of the present invention including those compounds represented by any one of Formula I-II are capable of stabilizing p53. Although not being bound by any theory, it is believed that preferred compounds of the invention can stabilize p53 activity in transformed cells by inhibition of MDM2 ubiquitin ligase activity. More particularly, it is believed that compounds of the invention, including those compounds of Formula I-II, are capable of inhibiting the ubiquitin ligase (E3) activity of MDM2.

Some compounds herein are commercially available or can be synthesized. As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2nd. Ed., Wiley-VCH Publishers (1999); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1999); and L. Paquette, ed., *Encyclopedia of Reagents for Organic Synthesis*, John Wiley and Sons (1995), and subsequent editions thereof.

Methods of Treating Disease

In one aspect, the invention provides a method of treating a subject suffering from or susceptible to a cell proliferative disorder or disease comprising: administering to the subject an effective amount of a compound or pharmaceutical composition of formula I or formula II.

In another aspect, the invention provides a method of treating or preventing cancer comprising administering a compound or pharmaceutical composition of formula I or II, to a subject suffering from or susceptible to cancer.

In one embodiment, the invention provides a method of treating or preventing cancer wherein the subject is suffering from a solid tumor or disseminated cancer. In another embodiment, the invention provides a method of treating or preventing cancer wherein subject has cancer cells that comprise a wild-type p53 gene. In another embodiment, the invention provides a method of treating or preventing cancer wherein the compound is capable of activating p53 mediated tumor suppression. In still another embodiment, the invention provides a method of treating or preventing cancer wherein the subject has a solid tumor. In yet another embodiment, the invention provides a method of treating or preventing cancer wherein the subject has a disseminated cancer.

In another embodiment, the invention provides a method of treating or preventing cancer wherein the compound or composition is administered alone or in combination with other anti-cancer or anti-tumor therapeutics.

In other embodiments, the subject is a mammal. In a further embodiment, the subject is a primate or human.

In another aspect, the invention provides a method of activating p53 mediated tumor suppression comprising contacting administering to mammalian cells a compound or pharmaceutical composition of formula I or II.

In certain embodiments, the cells are contacted in vitro. In other embodiments, the cells are contacted in vivo. In another embodiment, the compound or composition is administered to a mammal.

In certain aspects, the invention provides a method of treating against undesired cell proliferation comprising: administering to a mammal suffering from or susceptible to cancer the compound 5-(3-Dimethylamino-propylamino)-3,10-dimethyl-10H-pyrimido[4,5-b]quinoline-2,4-dione, and pharmaceutically acceptable salts thereof.

In another aspect, the invention provides a method of modulating HDM2 autoubiquitination in a subject, the method comprising the step of administering to the subject a compound of formula I or II, in an amount and under conditions sufficient to modulate HDM2 autoubiquitination. In certain embodiments, the modulation is down-regulation.

Particularly preferred compounds of the invention also may be selective for cancer cells relative to normal cells of a subject, i.e., such preferred compounds will exhibit reduced cell death in normal cells relative to targeted cancer cells. In particular, such preferred compounds can inhibit proliferation or induce apoptosis of targeted cancer cells, without exerting significant toxicity to normal (non-cancer) cells that may be contacted with the administered compound(s).

Compounds of the invention are useful for a number of therapeutic applications. In particular, the invention includes methods for treatment and prophylaxis of cancer, including cancers of the breast, lung, prostate, brain, liver, testes, skin, among others. Disseminated cancers (e.g., leukemias) as well as solid tumors may be treated by methods of the invention. Treatment methods of the invention may include administration of an effective amount of one or more compounds of the invention to cancer cells, such as those mentioned above. More particular methods include administering an effective amount of a compound of the invention to a subject such as a mammal, particularly a primate, e.g., a human that is suffering from or susceptible to (prophylactic treatment) abnormal cell proliferation, especially a cancer, such as a cancer mentioned above. Preferably, a subject is identified and selected that is susceptible or suffering undesired cell growth, especially cancer, such as a cancer mentioned above. An effective amount of one or more compounds of the invention suitably is an amount of one or more of the compounds of the invention sufficient to stabilize p53 in cells. The invention also includes use of one or more compounds disclosed herein, in combination or coordination with existing chemotherapies and/or radiotherapeutic protocols.

The invention also includes methods to stabilize p53 in cells, particularly mammalian cells, such as primate cells especially human cells.

Preferred methods of the invention are suitable for use in tumor growth regulation and comprise the administration of compounds of Formula I or II to targeted cells.

In a further aspect, the invention provides use of a compound of Formulae I or II, as defined herein, for the treatment or prevention (including prophylactic treatment) of a disease or condition as disclosed herein, including treatment or prevention of cancer or other undesired cell growth or proliferation.

In a yet further aspect, the invention provides use of a compound of Formulae I or II, as defined herein, for the preparation of a medicament for the treatment or prevention (including prophylactic treatment) of a disease or condition as disclosed herein, including treatment or prevention of cancer or other undesired cell growth or proliferation.

Particularly preferred compounds of the invention also may be selective for cancer cells relative to normal cells of a subject, i.e., such preferred compounds will exhibit reduced cell death in normal cells relative to targeted cancer cells. In particular, such preferred compounds can inhibit proliferation or induce apoptosis of targeted cancer cells, without exerting significant toxicity to normal (non-cancer) cells that may be contacted with the administered compound(s).

Preferred therapeutic methods of the invention include treating malignancies, including solid tumors and disseminated cancers. Exemplary tumors that may be treated in accordance with the invention include e.g. cancers of the lung, prostate, breast, liver, colon, breast, kidney, pancreas, brain, skin including malignant melanoma and Kaposi's sarcoma, testes or ovaries, or leukemias or lymphomia including Hodgkin's disease.

The present invention also comprises methods of modulating HDM2 autoubiquitination in a subject, which suitably comprise administering to the subject one or more compounds of Formulae I or II as set forth above in an amount and under conditions sufficient to modulate Hdm2 autoubiquitination. Preferably, the modulation is down-regulation. Effective dosage amounts and administration protocols can be readily determined empirically, e.g. by standard efficacy evaluations. Efficacy and thus Hdm2 autoubiquitination modulation can be assessed e.g. by therapeutic benefit as discussed herein, such as in vitro or in vivo treatment against cancer or viral infection.

Compounds of the invention also will be useful to probe the function of the ubiquitin system and in inhibiting non-proteasomal functions of ubiquitination. In addition to its role in proteasomal degradation of target proteins, the ubiquitin system is also involved in a number of cellular processes unrelated to proteasomal degradation including endocytosis, trafficking in the endosomal system, viral budding, DNA repair, nucleocytoplasmic trafficking and kinase activation. Prior to the preferred present compounds, there have been limited tools that allow probing of the role of the ubiquitin system in these processes.

The therapeutic methods of the invention generally comprise administration of an effective amount of one or more compounds of the invention to cells or a subject including a mammal, such as a primate, especially a human, in need of such treatment. The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The treatment methods of the invention also will be useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Therapeutic methods of the invention can also include the step of identifying that the subject is in need of treatment of diseases or disorders described herein, e.g., identifying that the subject is in need of treatment for cancer. The identification can be in the judgment of a subject or a health professional and can be subjective (e.g., opinion) or objective (e.g., measurable by a test or a diagnostic method). Tests for cancer are known and may include e.g. analysis of patient sample (e.g. biopsed tissue, or patient fluid such as blood, saliva, etc.) and for cancer cells or protein markers of a cancer. In each of these methods, a sample of biological material, such as blood, plasma, semen, or saliva, is obtained from the subject to be tested. Thus, the methods of the invention can include the step of obtaining a sample of biological material (such as a bodily fluid) from a subject; testing the sample to determine the presence or absence of a cell proliferative disease such as detectable cancer; and determining whether the subject is in need of treatment according to the invention.

The methods delineated herein can further include the step of assessing or identifying the effectiveness of the treatment or prevention regimen in the subject by assessing the presence, absence, increase, or decrease of a marker, including a marker or diagnostic measure of cancer or other proliferative disease; preferably this assessment is made relative to a measurement made prior to beginning the therapy. Such assessment methodologies are known in the art and can be performed by commercial diagnostic or medical organizations, laboratories, clinics, hospitals and the like. As described above, the methods can further include the step of taking a sample from the subject and analyzing that sample. The sample can be a sampling of cells, genetic material, tissue, or fluid (e.g., blood, plasma, sputum, etc.) sample. The methods can further include the step of reporting the results of such analyzing to the subject or other health care professional. The method can further include additional steps wherein (such that) the subject is treated for the indicated disease or disease symptom.

Compounds of the invention may be administered singularly (i.e., sole therapeutic agent of a regime) to treat or prevent diseases and conditions such as undesired cell proliferation and/or viral infection as disclosed herein.

Compounds of the invention also may be administered as a "cocktail" formulation, i.e., coordinated administration of one or more compounds of the invention together with one or more other active therapeutics.

For instance, for a chemotherapy application, one or more compounds of the invention including those of Formulae I or II may be administered in coordination with a regime of one or more other chemotherapeutic agents, particularly a compound that functions against cancer cells other than by p53 stabilization such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of the invention include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer.

A particularly suitable combination protocol may include coordinated administration of one or more compounds of the invention with a compound that can activate but not necessarily stabilize p53, e.g. a therapeutic agent that can enhance interaction of p53 with histone acetylases.

In another aspect, the invention provides a kit, comprising an effective amount of a compound of formula I or formula II, in unit dosage form, together with instructions for administering the compound to a subject suffering from or susceptible to a cell proliferative disorder.

Screening Assays

The compounds of the invention exhibit detectable inhibition of MDM2 E3 ubiquitin ligase activity in an in vitro assay (defined herein as a "standard MDM2 activity in vitro assay"), particularly a detectable decrease in MDM2 ubiquitination as measured by a decrease in the addition of ubiquitin molecules to MDM2 as assessed using an SDS-PAGE gel based means of assessment.

The invention further provides methods for identifying (e.g., through screening) other compounds possessing activity as anti-cancer agents. The assays are preferably based on measurement of inhibition of MDM2 ubiquitin ligase activity, such as by standard MDM2 activity in vitro assay. Potential inhibitors of MDM2 would regulate the stability and function of p53 and MDM2. Preferably the assays measure the self-ubiquitylation of MDM2 in the presence of candidate compounds. An increased inhibition of the self-ubiquitylation of MDM2 in the presence of candidate compounds, as compared to control samples is indicative of a potential anti-tumor compound. Preferably, a candidate compounds inhibits self-ubiquitylation of MDM2 by at least 20% greater as compared to a control (no candidate compound administered) as measured in a standard MDM2 activity in vitro assay, more preferably a candidate compound inhibits self-ubiquitylation of MDM2 by at least about 30%, 40%, 50%, 60%, 70%, 80%, 90% or 100% as compared to a control system (no candidate compound administered) as measured in a standard MDM2 activity in vitro assay. Additional in vitro assays of use in identifying agents include inhibition of p53 ubiquitination by MDM2 (described infra). In such an assay, p53 produced in human or mouse cells or translated in a cell free eukaryotic expression system is pre-bound to MDM2 and inhibition of p53 ubiquitination is assessed.

In another preferred embodiment, potential inhibitors of MDM2 that regulate the stability and function of p53, can be determined in a cell based assay. Potential inhibitors of MDM2 would regulate the stability and function of p53 and MDM2. Preferably, the assays measure number of cells undergoing apoptosis due to the inhibition of MDM2 induced p53 degradation in tumor cells in the presence and/or absence of candidate compounds as compared to normal cells in the presence and/or absence of candidate compounds. The assay can also measure stabilization of p53 and MDM2 in cells following treatment with one or more candidate compounds.

In such assays of the invention, an increase in the number of cells undergoing apoptosis in the presence of candidate compounds in tumor cells, as compared to normal untreated cells is indicative of a potential anti-tumor compound. Preferably a candidate compound increases apoptosis of tumor cells by at least 20% as compared to a control system (no candidate compound administered), more preferably a candidate compound increases apoptosis of a tumor cell by at least about 30%, 40%, 50%, 60%, 70%, 80%, 90% or 100% as compared to a control system (no candidate compound administered). That is, for example, 80% increase of apoptosis refers to number of cells still surviving as compared to the controls. Apoptosis is preferably measured by visual observation (e.g., blebbing or trypan blue retention). Nucleic acids from cells having undergone apoptosis can be run on gels showing the characteristic 200 bp nucleic acid ladder that is indicative of cells having undergone apoptosis, or cells with less than a G1 DNA content can be identified by fluorescence activated cell sorting. Other assays for apoptosis include TUNEL assays or detection of caspase activation or trypan blue exclusion.

Assays of the invention also are useful for assessing MDM2 inhibition in in vitro and in vivo systems. The invention also provides methods (also referred to herein as "screening assays") for identifying candidate compounds useful for treatment against cancer cells or other undesired cell proliferation. Screening assays can be adapted to a high throughput format to enable the rapid screening of a large number of compounds. Assays and screening methods can be used for identification of compounds possessing MDM2-specific and/or general inhibition of ubiquitin enzyme inhibitory activity. Thus, in accordance with the invention, methods are provided to screen candidate compounds which exhibit potential anti-cancer activity by measuring p53 stability in transformed cells and/or apoptosis and cell death.

MDM2 protein binds tumor suppressor p53 and targets it for ubiquitylation and proteosome-mediated degradation. MDM2 is a RING finger-containing E3 ubiquitin ligase for p53. MDM2 also catalyzes self-ubiquitylation, and thus regulates intracellular levels of both p53 and itself. Without wishing to be bound by theory, molecules which inhibit the binding of MDM2 to p53 could be used to identify drug compounds that inhibit MDM2 ligase activity that affects p53 stability. Similarly, interference with the expression of MDM2 by a candidate drug compound can identify anti-tumor compounds that can be further analyzed using a high-throughput assay described below. As a theoretical illustrative example, expression may be down regulated by administering small molecules and peptides which specifically inhibit MDM2 expression can also be used.

In theory, such inhibitory molecules can be identified by screening for interference of the MDM2/p53 interaction where one of the binding partners is bound to a solid support and the other partner is labeled. Antibodies specific for epitopes on MDM2 or p53 which are involved in the binding interaction will interfere with such binding. Solid supports which may be used include any polymers which are known to bind proteins. The support may be in the form of a filter, column packing matrix or sephadex beads. Labeling of proteins can be accomplished according to many techniques. Radiolabels, enzymatic labels, and fluorescent labels can be used. Alternatively, both MDM2 and p53 may be in solution and bound molecules separated from unbound subsequently. Any separation technique may be employed, including immunoprecipitation or immunoaffinity separation with an antibody specific for the unlabeled binding partner.

For in vitro assays MDM2 can be expressed as a GST fusion. This allows for a high level of expression of protein that can be purified on glutathione Sepharose. Detection of ubiquitination of MDM2 can be accomplished, for example, using $^{32}$P-labeled ubiquitin, Western blotting with anti-ubiquitin, or by looking at a shift in the molecular weight of GST fusion by Western blotting with anti-GST. A variety of in vitro assays that measure levels of self-ubiquitylated MDM2 can be employed, such as for example, immunoprecipitation of ubiquitylated MDM2; gel assays wherein the amount of ubiquitylated MDM2 is measured by densitometric scanning or where covalent attachment of radio-labeled or otherwise tagged ubiquitin to MDM2 or p53 is measured; Western blot analysis, or other known techniques such as ELISA, immunoprecipitation, RIA, and the like. Candidate compounds that inhibit self-ubiquitylation of MDM2, as described in detail in the Examples which follow, are detected by a shift in molecular weight either of MDM2 or of ubiquitin that becomes covalently attached to MDM2. (See for example Lorrick K L., et al., Proc. Natl. Acad. Sci. USA, 1999, 96:11364-11369; Fang S., et al., J. Biol. Chem., 2000, 275(12)8945-8951; Ryan K M., et al., Curr. Op. Cell Biol., 2001, 13:332-337; which are herein incorporated by reference in their entirety). MDM2 self-ubiquitylation assays are run (see for example the results shown in FIGS. 2 and 3) in the presence or absence of a known amount of candidate compound. An aliquot of each of the test and control reactions are run on a standard SDS-PAGE gel. Test reactions whereby the candidate compounds inhibit the self-ubiquitylation of MDM2 will have a decrease in high molecular weight ubiquitylated MDM2.

In cellular assays, endogenous or transfected MDM2 is used. For transfected MDM2, ubiquitination is evaluated by an upward smear by anti-MDM2 Western blotting after resolution of cell lysates on SDS-PAGE. Alternatively, immunoprecipitation can be accomplished by subjecting lysates from cells (treated and untreated cells) to anti-MDM2, followed by Western Blotting and detecting ubiquitination by using anti-ubiquitin antibodies. Preferred screening methods comprise identifying a candidate compound based on assessment of p53 stabilization (e.g. half life of p53) and steady state levels, and the level of MDM2, as compared to a control, e.g. normal (non-cancer cells).

Steady-state levels of p53 and MDM2 in the cells can be determined by a number of approaches. For instance, lysates containing cellular protein can be immuno-precipitated with, for example, a rabbit anti-p53 polyclonal serum or MDM2 polyclonal serum, blotted onto polyvinylidenedifluoride (PVDF) membranes and probed with a monoclonal antibody cocktail comprising, for example, monoclonal antibodies to various epitopes of p53, or MDM2. Such antibodies are commercially available. Immunoblot analyses of cellular extracts, taken at different time points after treatment with a candidate compound is determinative of the half-life of p53 as compared to normal controls. Thus, increase or decrease in levels of p53 over periods of time is determinative of p53 stability based on its half-life and steady state levels. The lysates can be further purified, for example, by immunoprecipitation of p53 and/or MDM2 directly or indirectly of MDM2 and p53, or by affinity chromatography. Thus, candidate compounds that inhibit MDM2 ubiquitin ligase activity, can be screened for any effect on p53 stability.

Cell-based assays include model systems where primary human epithelial cells ("normal cells") are compared to the same cells expressing the adenovirus E1A oncogene ("transformed cells"). Activation of p53 was not toxic to normal cells, but activation of p53 in transformed cells induces p53-mediated apoptosis. High concentrations of wild type (wt) p53 protein can induce apoptosis in a variety of different tumor cells. Potential inhibitors of MDM2 would regulate the stability and function of p53 and MDM2. Preferably the assays measure number of cells undergoing apoptosis due to MDM2 induced p53 degradation in tumor cells in the presence or absence of candidate compounds as compared to normal cells in the presence or absence of candidate compounds. An increase in the number of these cells undergoing apoptosis in the presence of candidate compounds in tumor cells, as compared to normal untreated cells is indicative of a potential anti-tumor compound. Preferably a candidate compound increases apoptosis of tumor cells by at least 20% as compared to a control (no candidate compound administered), more preferably a candidate compound increases apoptosis of a tumor cell by at least about 30%. 40%, 50%, 60%, 70%, 80%, 90% or 100% as compared to a control (no candidate compound administered). That is, for example 80% increase of apoptosis refers to a decrease in the numbers of cells still surviving as compared to the controls.

Apoptosis can be measured by a variety of techniques. For example, apoptosis can be measured by determination of cell phenotype. Phenotype refers to how the cell looks, typically microscopically, but gross or macroscopic appearance can be observed. The phenotype changes depending on the growth rate of the cells. For instance, the microscopic morphology of cells that are rapidly dividing and growing is different than that of cells undergoing cell death by apoptosis. Determination of cell phenotype is well within the ability of one of ordinary skill in the art.

There are also a number of biochemical assays that can be used to detect apoptosis, such as "laddering" of the cellular DNA. When testing compounds for the ability to induce apoptosis, cell death (not cytostasis) is an endpoint of a compound application to the cell. A classic signature of apoptosis is the cleavage of nuclear DNA into nucleosomal subunits. On gels, this gives rise to the appearance of a ladder as nucleosomal units are sequentially cleaved from DNA. Observation of a classic DNA ladder is indicative of apoptosis. For example, cells are lysed and the high molecular weight DNA is removed by centrifugation. The aqueous phase is treated with proteinase K to digest proteins. After a phenol/chloroform extraction, the pellet is dissolved in deionized water and treated with 500 µg/ml RNaseA. The DNA is run on a 2% agarose minigel. Observation for a classic DNA ladder is made and a photograph can be taken. Cell death is verified by the demonstration of DNA as represented by the ladder configurations on the gel (see for example, White E., et al. 1984, J. Virol. 52:410). There are also a variety of other assays available for apoptosis such as "TUNEL" assays (see Gavrieli, Y., et al. (1992) J. Cell. Biol. 119:493).

As discussed above, the invention assays and screening methods for identification of other compounds possessing anti-cancer activity, including MDM2-specific and/or general inhibition of ubiquitin enzyme inhibitory activity. Thus, in accordance with the invention, methods are provided to screen candidate compounds which exhibit potential anti-cancer activity by measuring p53 stability in transformed cells and/or apoptosis and cell death.

Pharmaceutical Compositions

In certain aspects, the invention provides a pharmaceutical composition comprising the compound of formula I or formula II, and a pharmaceutically acceptable carrier. In one embodiment, the invention provides a pharmaceutical composition comprising 5-(3-Dimethylamino-propylamino)-3,10-dimethyl-10H-pyrimido[4,5-b]quinoline-2,4-dione or its hydrochloride salt, and a pharmaceutically acceptable carrier. In certain embodiments, the invention provides a pharmaceutical composition further comprising an additional therapeutic agent. In other embodiments, the invention provides a pharmaceutical composition wherein the additional therapeutic agent is an anticancer agent.

Pharmaceutical compositions of the invention include a compound of the invention packaged together with instructions (written) for therapeutic use of the compound, particularly to treat a subject suffering from or susceptible to cancer. Most preferred method of treating the patient with the pharmaceutical compositions of the invention, is administration of the compositions intravenously. However, other routes of administration of the pharmaceutical compositions can be used.

Compounds of the invention can be administered by a variety of routes, such as orally or by injection, e.g., intramuscular, intraperitoneal, subcutaneous or intravenous injection, or topically such as transdermally, vaginally and the like.

In a preferred embodiment, the compounds of the invention are administered intravenously. Compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g. a carboxy group, base additional salts may be prepared. Lists of additional suitable salts may be found, e.g., in Remington's Pharmaceutical Sciences, $17^{th}$ ed., Mack Publishing Company, Easton, Pa.

For oral administration, pharmaceutical compositions containing one or more compounds of the invention may be formulated as e.g. tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampoules are convenient unit dosages.

Compounds of the invention may be administered singularly (i.e., sole therapeutic agent of a regime) to treat or prevent diseases and conditions such as undesired cell proliferation as disclosed herein.

Compounds of the invention also may be administered as a "cocktail" formulation, i.e., coordinated administration of one or more compounds of the invention together with one or more other active therapeutics. For instance, one or more compounds of the invention may be administered in coordination with a regime of one or more other chemotherapeutic agents, particularly a compound that functions against cancer cells other than by p53 stabilization such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of the invention include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer.

A particularly suitable combination protocol may include coordinated administration of one or more compounds of the invention with a compound that can activate but not necessarily stabilize p53, e.g. a therapeutic agent that can enhance interaction of p53 with histone acetylases.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Pharmaceutical compositions of the invention include a compound of the invention packaged together with instructions (written) for therapeutic use of the compound, particularly to treat a subject suffering from or susceptible to cancer. Most preferred method of treating the patient with the pharmaceutical compositions of the invention, is administration of the compositions intravenously. However, other routes of administration of the pharmaceutical compositions can be used.

The actual amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also *Remington's Pharmaceutical Sciences*, supra. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day; or any dosage range in which the low end of the range is any amount between 0.01 mg/kg/day and 90 mg/kg/day and the upper end of the range is any amount between 1 mg/kg/day and 100 mg/kg/day (e.g., 0.5 mg/kg/day and 2 mg/kg/day, 5 mg/kg/day and 20 mg/kg/day). The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage; or any dosage range in which the low end of the range is any amount between 0.05 mg/day and 400 mg/day and the upper end of the range is any amount between 1 mg/day and 500 mg/day (e.g., 5 mg/day and 100 mg/day, 150 mg/day and 500 mg/day).

A "pharmaceutically acceptable derivative or prodrug" means any pharmaceutically acceptable salt, ester, salt of an ester, or other derivative of a compound of this invention which, upon administration to a recipient, is capable of providing (directly or indirectly) an active compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30,451454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214.

The invention also provides kits for treatment or prevention of a disease or disorder (or symptoms) thereof associated with cell proliferation. In one embodiment, the kit includes an effective amount of a compound herein in unit dosage form, together with instructions for administering the compound to a subject suffering from or susceptible to a disease or disorder or symptoms thereof associated with cell proliferation, wherein the effective amount of a compound is as described herein. In preferred embodiments, the kit comprises a sterile container which contains compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the compound for treatment of a disease or disorder or symptoms thereof associated with cell proliferation, including treatment of cell proliferative diseases and disorders; in preferred embodiments, the instructions include at least one of the following: description of the compound; dosage schedule and administration for treatment of a disease or disorder or symptoms; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

This invention is further illustrated by the following examples which should not be construed as limiting.

Example 1

Compound 1 Accumulates Hdm2 and p53 in Non-Transformed Cells

Human retina pigment epithelial (RPE) cells were cultured with HyQ DME/F (HyClone) supplemented with 10% FCS and 2.5% Sodium Bicarbonate. They were harvested with Trpsin-EDTA and seeded into a 12-well tissue culture cluster and incubated for 18-40 hours to reach 80% confluent. Following treatment with indicated compounds for 8 hours, the cells were harvested and lysed with RIPA buffer. Following removal of insoluble pellet by centrifugation for 20 minutes at 10000 rpm, the lysate was separated on a 4-20% gradient SDS-polyacrylamide gel and transferred onto nitrocellulose membrane. The membrane was then blotted with anti-p53 antibody (DO-1) anti-Hdm2 antibodies (Ab-1 and Ab-2). After extensive washing with PBS containing 0.5% Triton x-100, it was incubated with HRP-conjugated donkey anti-mouse antibody and visualized using enhanced chemiluminescence. Compound 1 showed significant accumulation of both Hdm2 and p53, when dissolved in a 5 μM or 10 μM solution in PBS, or a 5 μm solution in DMSO (FIG. 1).

Example 2

Compound 1 Stabilizes Transfected Hdm2 in p53-/-Mdm2-/- Cells

Figure 2:
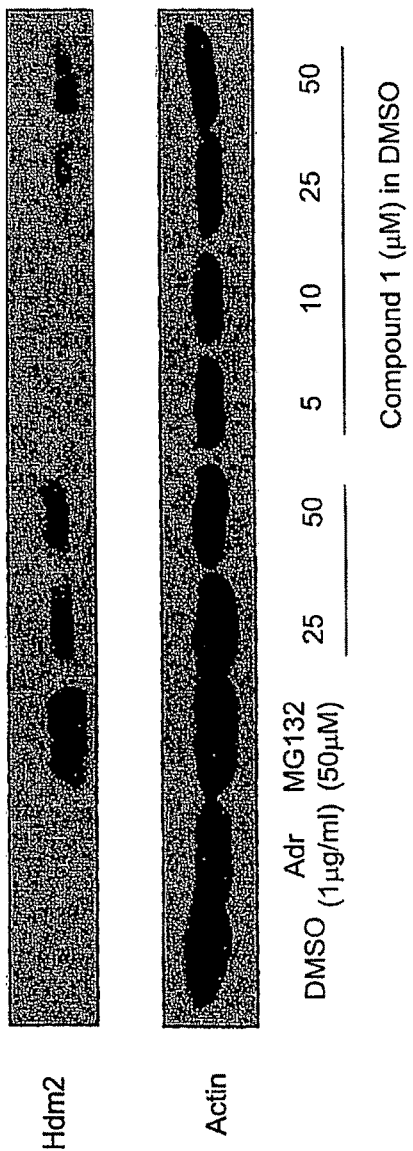
FIG. 2 shows the stabilization of transfected Hdm2 by compound 1.

MEFs from p53 and mdm2-deficient mice were transfected with a CMV-driven Hdm2-expressing construct. After 24 hours, the cells were treated with indicated compounds for 8 hours and harvested for immunobloting with anti-Hdm2 antibody. Anti-β-actin blot was also performed. It was found that compound 1 increases Hdm2 levels in a dose-dependent manner, with doses of compound 1 administered in concentrations of 5 μM, 10 μM, 25 μM, and 50 μM in DMSO (FIG. 2).

Example 3

P53 Accumulated by Compound 1 is Transcriptionally Active

Figure 3:
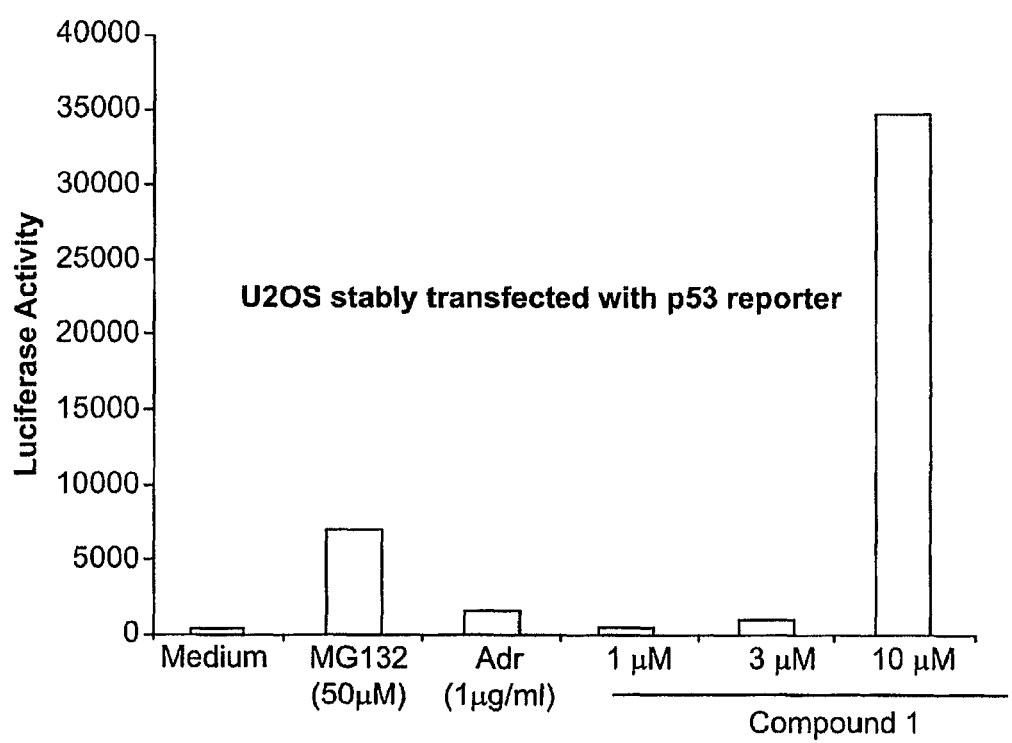
FIG. 3 shows the activation of p53 by compound 1.

U2OS cells stably transfected with a p53 response element-driven luciferase were treated with indicated concentration of compounds for 18 hours. The cells were then harvested and lysed to measure luciferase activity using the luciferase assay system (Promega) according to manufacturer's instruction. It was observed that compound 1 demonstrated a high capacity to activate a p53 reporter in cells that express p53. As can be seen in FIG. 3, at a concentration of 10 μM, the activity of compound 1 is much greater than proteosome inhibitor and Adriamycin.

Example 4

Compound 1 Selectively Induces Apoptosis in Transformed Cells

Figure 4:
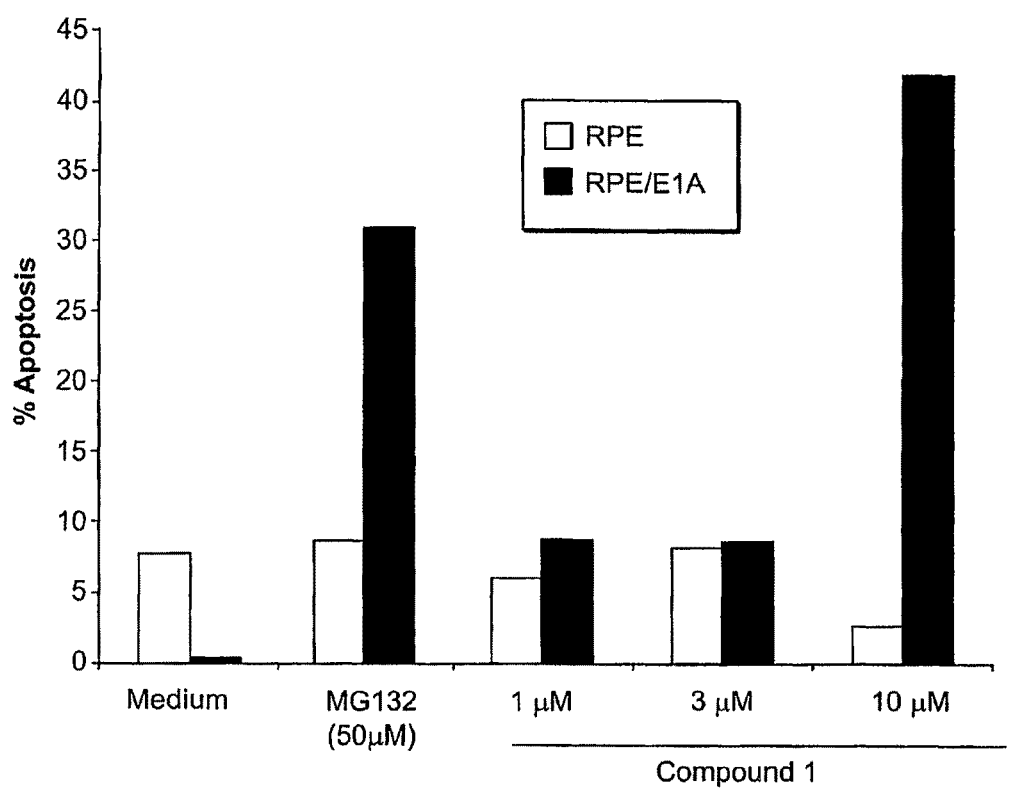
FIG. 4 shows the capacity of compound 1 to induce apoptosis in transformed cells relative to non-transformed cells.

RPE and RPE cells transformed with E1A were treated with indicated concentration of compound for 20 hours. The percentages of cells with sub-G1 DNA content were measured using a FACSCalibur (Becton Dickinson). As can be seen in FIG. 4, compound 1 induces apoptosis in transformed cells relative to non-transformed cells.

Example 5

Compound 1 Specificity Towards Hdm1/Mdm1

Figure 5:
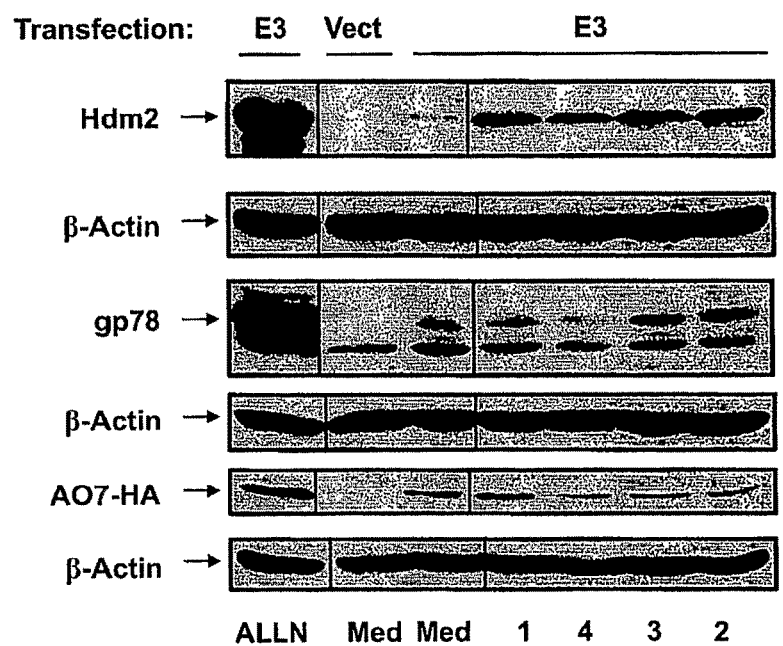
FIG. 5 shows that compound 1 significantly increased the level of Hdm2, and has selectivity toward Hdm2.

Experiments were carried out to further characterize the specificity of compound 1 in stabilizing different E3s to ascertain its specificity towards Hdm2/Mdm2. In FIG. 5, mouse embryonic fibroblasts (MEFs) that express neither Mdm2 nor p53 were transfected with empty vector or plasmids encoding three different RING finger E3s Hdm2, gp78 (AMFR) or AO7 (RNF25). Following treatment with ALLN, 1, 2 (10-(4-methyl-phenyl)-7-nitro-10H-pyrimido[4,5-b]quinoline-2,4-dione), 3 (10-(4-chloro-phenyl)-7-nitro-10H-pyrimido[4,5-b]quinoline-2,4-dione), and 4 (10-(3-chloro-phenyl)-7-nitro-10H-pyrimido[4,5-b]quinoline-2,4-dione), levels of the E3s were examined by immunoblotting with specific antibodies. As is evident, compound 1 significantly increased the level of Hdm2, but had little effects on the level of gp78 or AO7. These results indicate that compound 1 has selectivity toward Hdm2. Compounds 2-4 refer to compounds previously characterized as non-water soluble inhibitors (U.S. Ser. No. 10/545,547); ALLN is a peptide aldehyde proteasome inhibitor. As expected, the proteasome inhibitor resulted in higher levels of all of these E3s—this is consistent with their constitutive ubiquitin-mediated turnover.

Example 6

Ability of Compound 1 to Affect Hdm2-Mediated Ubiquitylation

Figure 6:
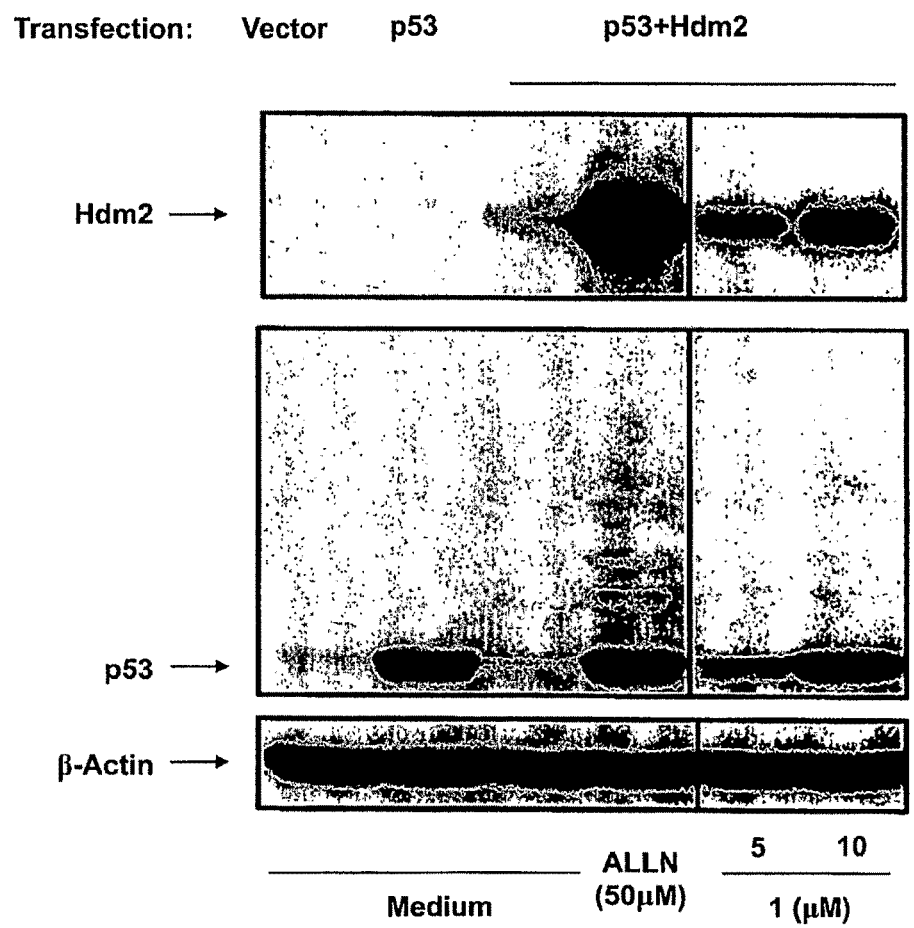
FIG. 6 shows an evaluation of the ability of compound 1 to affect Hdm2-mediated ubiquitylation and degradation of p53 and Hdm2 in U2OS cells.

An evaluation of the ability of compound 1 to affect Hdm2-mediated ubiquitylation and degradation of p53 and Hdm2 in U2OS cells was carried out, and the results are demonstrated in FIG. 6. The degradation of both proteins was prevented by the new inhibitor. As expected, the proteasome inhibitor (ALLN) also stabilized Hdm2 and p53. Notably, ubiquitylated p53 was easily detectable with proteasome inhibitor treatment. In contrast, no ubiquitylated p53 accumulated upon treatment with compound 1. This is consistent with compound 1 functioning by inhibiting ubiquitylation of p53.

Example 7

Preferential Killing of Tumor Cells Expressing Wild Type p53

Figure 7:
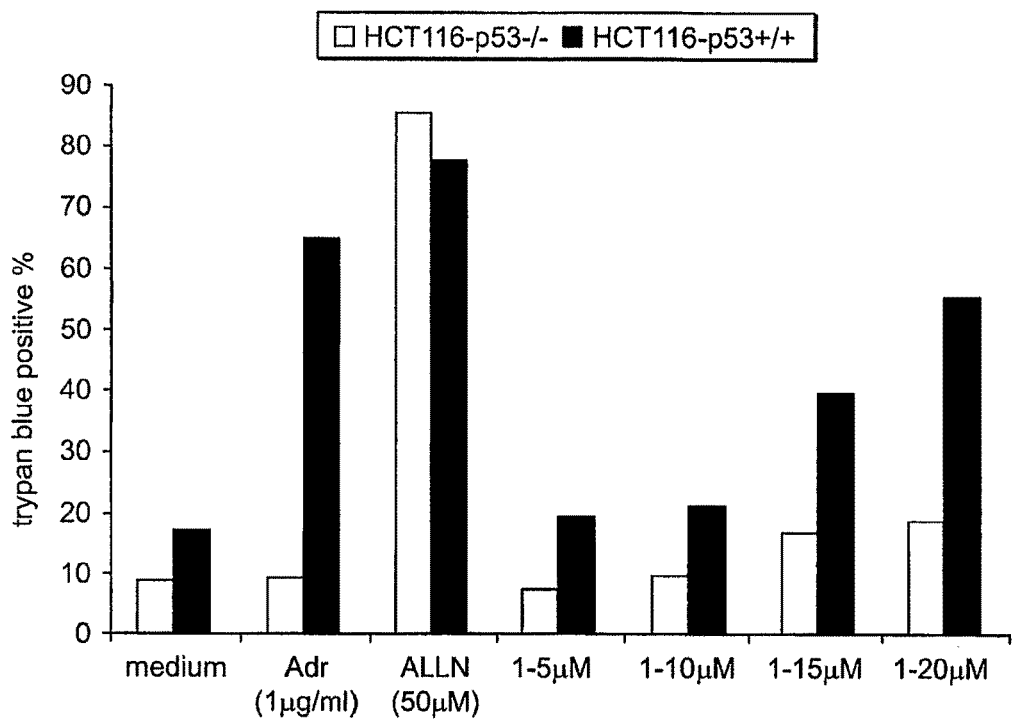
FIG. 7 shows the preferential killing of tumor cells expressing wild type p53.

An assessment of the apoptosis-inducing activity of compound 1 in tumor cells was carried out. In FIG. 7 a pair of cell lines that that either do or do not express p53, was examined. As with cells that have been specifically transformed by expression of oncogenes (described in U.S. Ser. No. 10/545,547), compound 1 exhibits preferential killing of tumor cells expressing wild type p53. Additional experiments have ruled out the possibility that compound 1 is functioning by inducing DNA damage (data not shown).

The foregoing description of the invention is merely illustrative thereof, and it is understood that variations and modifications can be effected without departing from the spirit or scope of the invention as set forth in the following claims.

The contents of all references (including literature references, issued patents, published patent applications, and co-pending patent applications) cited throughout this application are hereby expressly incorporated herein in their entireties by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:
1. A method of treating a subject suffering from colon cancer, comprising
   determining that the subject has cancer cells that comprise a wild type p53 gene, and
   administering to the subject an effective amount of a compound according to Formula I:

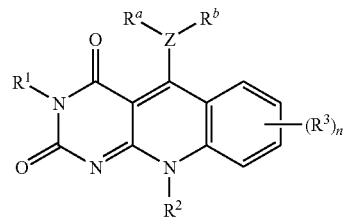

wherein:
$R^1$ is selected from the group consisting of hydrogen, optionally substituted alkyl, optionally substituted alkenyl, optionally substituted alkynyl, optionally substituted carbocyclic aryl, optionally substituted heteroaryl, optionally substituted cycloalkyl, or optionally substituted heteroalicyclic;
$R^2$ is selected from the group consisting of optionally substituted alkyl, optionally substituted cycloalkyl, or optionally substituted heteroalicyclic;
$R^3$ is, for each occurrence, selected from the group consisting of H, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl amino, optionally substituted cycloalkyl, optionally substituted heteroalicyclic, optionally substituted aminoalkyl, —OR$^a$, —NR$^a$R$^b$, —S(O)$_q$R$^a$, —C(O)R$^a$, —OC(O)R$^a$, —NR$^a$C(O)R$^a$—C(S)R$^a$, —OC(S)R$^a$, —SC(S)R$^a$, —NR$^a$C(S)R$^a$, —C(NR$^a$)R$^a$, —OC(NR$^a$)R$^a$, —SC(NR$^a$)R$^a$, —NR$^a$SO$_2$R$^c$, —OS(O)$_2$R$^a$;
Z is selected from N, O, or S(O)$_q$; wherein R$_a$ is absent if not allowed;
R$^a$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, hydroxylalkyl, alkylcarbonylalkyl, mercaptoalkyl, aminoalkyl, sulfonylalkyl, sulfonylaryl, or thioalkoxy;

$R^b$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted araalkyl, an optionally substituted heteroaralkyl, an optionally substituted aryl, an optionally substituted heteroaryl, haloalkyl, —$(CH_2)_nOR^c$, —$(CH_2)_nSR^c$, —$(CH^2)_nNR^cR^c$, hydroxylalkyl, alkylcarbonylalkyl, mercaptoalkyl, aminoalkyl, sulfonylalkyl, sulfonylaryl, or thioalkoxy;

$R^c$, for each instance is independently selected from the group consisting of H or an optionally substituted alkyl;

n is an integer from 0 to 3;

q is an integer from 0 to 2;

or a pharmaceutically acceptable salt thereof.

2. A method of treating a subject suffering from colon cancer, comprising administering to the subject an effective amount of a compound according to Formula II:

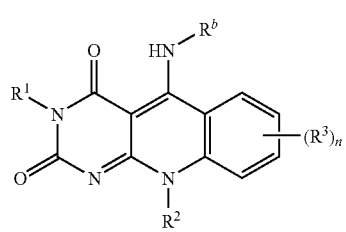

wherein:

$R^1$ is selected from the group consisting of optionally substituted alkyl, optionally substituted carbocyclic aryl, optionally substituted heteroaryl, or optionally substituted cycloalkyl;

$R^2$ is optionally substituted alkyl;

$R^3$ is, for each occurrence, selected from the group consisting of hydrogen, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl amino, optionally substituted cycloalkyl, optionally substituted heteroalicyclic, optionally substituted aminoalkyl, —$OR^a$, —$NR^aR^b$, —$S(O)_qR^a$, —$C(O)R^a$, —$OC(O)R^a$, —$NR^aC(O)R^a$, —$C(S)R^a$, —$OC(S)R^a$, —$SC(S)R^a$, —$NR^aC(S)R^a$, —$C(NR^a)R^a$, —$OC(NR^a)R^a$, —$SC(NR^a)R^a$, —$NR^aSO_2R^c$, —$OS(O)_2R^a$;

$R^a$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, hydroxylalkyl, alkylcarbonylalkyl, mercaptoalkyl, aminoalkyl, sulfonylalkyl, sulfonylaryl, or thioalkoxy;

$R^b$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted araalkyl, an optionally substituted heteroaralkyl, an optionally substituted aryl, an optionally substituted heteroaryl, haloalkyl, —$(CH_2)_nOR^c$, —$(CH_2)_nSR^c$, —$(CH^2)_nNR^cR^c$, hydroxylalkyl, alkylcarbonylalkyl, mercaptoalkyl, aminoalkyl, sulfonylalkyl, sulfonylaryl, or thioalkoxy;

$R^c$, for each instance is independently selected from the group consisting of H or an optionally substituted alkyl;

n is an integer from 0 to 3;

q is an integer from 0 to 2;

or a pharmaceutically acceptable salt thereof.

3. The method of claim 1 wherein $R^1$ is an optionally substituted alkyl

4. The method of claim 3, wherein $R^1$ is methyl.

5. The method of claim 1, wherein Z is N.

6. The method of claim 1, wherein $R^a$, for each instance, is independently H, an optionally substituted alkyl, an optionally substituted aryl, or an optionally substituted heteroaryl.

7. The method of claim 6, wherein $R^a$ is H.

8. The method of claim 1, wherein $R^b$, for each instance is independently selected from the group consisting of —$(CH_2)_nOR^c$, —$(CH_2)_nSR^c$, —$(CH^2)_nNR^cR^c$, hydroxylalkyl, alkylcarbonylalkyl, mercaptoalkyl, aminoalkyl, sulfonylalkyl, sulfonylaryl, or thioalkoxy.

9. The method of claim 8, wherein $R^b$ is —$(CH_2)nNR^cR^c$.

10. The method of claim 1, wherein each $R^c$ is independently an optionally substituted alkyl.

11. The method of claim 10, wherein $R^c$ is methyl.

12. The method of claim 1, where $R^2$ is selected from the group consisting of optionally substituted alkyl, optionally substituted cycloalkyl, or optionally substituted heteroalicyclic.

13. The method of claim 1 comprising administering a pharmaceutical composition comprising the compound of claim 1 and a pharmaceutically acceptable carrier.

14. The method of claim 13 wherein the pharmaceutical composition comprises 5-(3-Dimethylamino-propylamino)-3,10-dimethyl-10H-pyrimido[4,5-b]quinoline-2,4-dione or its hydrochloride salt, and a pharmaceutically acceptable carrier.

15. The method of claim 13, wherein the pharmaceutical composition further comprises an additional therapeutic agent.

16. The method of claim 1 wherein the compound is 5-(3-Dimethylamino-propylamino)-3,10-dimethyl-10H-pyrimido[4,5-b]quinoline-2,4-dione or a pharmaceutically acceptable salt thereof.

17. A method of modulating HDM2 autoubiquitination in a subject suffering from colon cancer, the method comprising the step of determining that the subject has cancer cells that comprise a wild type p53 gene, and administering to the subject a compound of claim 1, in an amount and under conditions sufficient to modulate HDM2 autoubiquitination in vitro.

18. The method of claim 17 wherein the modulation is down-regulation.

19. A kit comprising an effective amount of a compound of Formula I:

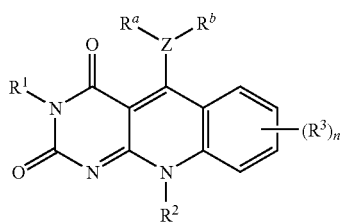

wherein:
$R^1$ is selected from the group consisting of hydrogen, optionally substituted alkyl, optionally substituted alkenyl, optionally substituted alkynyl, optionally substituted carbocyclic aryl, optionally substituted heteroaryl, optionally substituted cycloalkyl, or optionally substituted heteroalicyclic;

$R^2$ is selected from the group consisting of optionally substituted alkyl, optionally substituted cycloalkyl, or optionally substituted heteroalicyclic;

$R^3$ is, for each occurrence, selected from the group consisting of H, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl amino, optionally substituted cycloalkyl, optionally substituted heteroalicyclic, optionally substituted aminoalkyl, —$OR^a$, —$NR^aR^b$, —$S(O)_qR^a$, —$C(O)R^a$, —$OC(O)R^a$, —$NR^aC(O)R^a$, —$C(S)R^a$, —$OC(S)R^a$, —$SC(S)R^a$, —$NR^aC(S)R^a$, —$C(NR^a)R^a$, —$OC(NR^a)R^a$, —$SC(NR^a)R^a$, —$NR^aSO_2R^c$, —$OS(O)_2R^a$;

Z is selected from N, O, or $S(O)_q$; wherein $R_a$ is absent if not allowed;

$R^a$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted aralkyl, an optionally substituted heteroaralkyl, an optionally substituted aryl, an optionally substituted heteroaryl, haloalkyl, hydroxylalkyl, alkylcarbonylalkyl, mercaptoalkyl, aminoalkyl, sulfonylalkyl, sulfonylaryl, or thioalkoxy;

$R^b$, for each instance is independently selected from the group consisting of H, an optionally substituted alkyl, an optionally substituted alkenyl, an optionally substituted alkynyl, an optionally substituted cycloalkyl, an optionally substituted heterocycloalkyl, an optionally substituted araalkyl, an optionally substituted heteroaralkyl, an optionally substituted aryl, an optionally substituted heteroaryl, haloalkyl, —$(CH_2)_nOR^c$, —$(CH_2)_nSR^c$, —$(CH^2)_nNR^cR^c$, hydroxylalkyl, alkylcarbonylalkyl, mercaptoalkyl, aminoalkyl, sulfonylalkyl, sulfonylaryl, or thioalkoxy;

$R^c$, for each instance is independently selected from the group consisting of H or an optionally substituted alkyl;
n is an integer from 0 to 3;
q is an integer from 0 to 2;

in unit dosage form, together with instructions for administering the compound to a subject suffering from colon cancer and determined to have cancer cells that comprise a wild type p53 gene.

20. A method of treating a subject suffering from colon cancer, comprising
determining that the subject has cancer cells that comprise a wild type p53 gene, and
administering to the subject an effective amount of a compound according to Formula I:

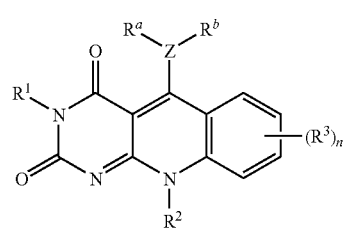

wherein:
$R^1$ is selected from the group consisting of hydrogen, optionally substituted alkyl, optionally substituted alkenyl, optionally substituted alkynyl, optionally substituted carbocyclic aryl, optionally substituted heteroaryl, optionally substituted cycloalkyl, or optionally substituted heteroalicyclic;

$R^2$ is methyl;

$R^3$ is, for each occurrence, selected from the group consisting of H, amino, hydroxy, cyano, nitro, carboxylate, carboxamide, optionally substituted alkyl, optionally substituted alkenyl, optionally substituted alkynyl, optionally substituted carbocyclic aryl, optionally substituted heteroaryl, optionally substituted alkoxy, optionally substituted mono- or di-alkyl amino, optionally substituted cycloalkyl, optionally substituted heteroalicyclic, optionally substituted aminoalkyl, —$OR^a$, —$NR^aR^b$, —$S(O)_qR^a$, —$C(O)R^a$, —$OC(O)R^a$, —$NR^aC(O)R^a$, —$C(S)R^a$, —$OC(S)R^a$, —$SC(S)R^a$, —$NR^aC(S)R^a$, —$C(NR^a)R^a$, —$OC(NR^a)R^a$, —$SC(NR^a)R^a$, —$NR^aSO_2R^c$, —$OS(O)_2R^a$;

Z is selected from N, O, or $S(O)_q$; wherein $R_a$ is absent if not allowed;
$R_a$ is hydrogen;
$R^b$ is —$(CH_2)nNR^cR^c$;
$R^c$, for each instance is independently selected from the group consisting of H or an optionally substituted alkyl;
n is an integer from 0 to 3;
q is an integer from 0 to 2;
or a pharmaceutically acceptable salt thereof.

21. A method claim 20, wherein the compound is 5-(3-Dimethylamino-propylamino)-3,10-dimethyl-10H-pyrimido[4,5-b]quinoline-2,4-dione hydrochloride salt.

* * * * *